US012702575B2

(12) United States Patent
Georgarakis et al.

(10) Patent No.: US 12,702,575 B2
(45) Date of Patent: Aug. 11, 2026

(54) ORTHOSIS AND METHOD FOR STABILIZING THE POSITION OF THE SCAPULA, SYSTEM FOR MOVING AN ARM AND METHOD FOR LIFTING A LOAD

(71) Applicant: ETH ZÜRICH, Zürich (CH)

(72) Inventors: Anna-Maria Georgarakis, Zurich (CH); Yves Dominic Zimmermann, Wettingen (CH); Robert Riener, Zurich (CH)

(73) Assignee: ETH ZÜRICH, Zurich (CH)

( * ) Notice: Subject to any disclaimer, the term of this patent is extended or adjusted under 35 U.S.C. 154(b) by 687 days.

(21) Appl. No.: 17/917,525

(22) PCT Filed: Apr. 6, 2021

(86) PCT No.: PCT/EP2021/058893
§ 371 (c)(1),
(2) Date: Oct. 6, 2022

(87) PCT Pub. No.: WO2021/204775
PCT Pub. Date: Oct. 14, 2021

(65) Prior Publication Data

US 2023/0138494 A1 May 4, 2023

(30) Foreign Application Priority Data

Apr. 7, 2020 (EP) .................................... 20168373

(51) Int. Cl.
*A61F 5/01* (2006.01)
*A61F 5/37* (2006.01)

(52) U.S. Cl.
CPC ........... *A61F 5/0102* (2013.01); *A61F 5/013* (2013.01); *A61F 5/3753* (2013.01)

(58) Field of Classification Search
CPC ...... A61F 5/0102; A61F 5/0118; A61F 5/013; A61F 5/37; A61F 5/3715; A61F 5/3723; A61F 5/373; A61F 5/3753
See application file for complete search history.

(56) References Cited

U.S. PATENT DOCUMENTS 2,310,566 A * 2/1943 Anderson ............ A61F 5/3753 602/19
3,945,376 A 3/1976 Kuehnegger
(Continued)

OTHER PUBLICATIONS

International Search Report and Written Opinion for PCT Application No. PCT/EP2021/058893 mailed Jun. 9, 2021.
(Continued)

*Primary Examiner* — Keri J Nelson
(74) *Attorney, Agent, or Firm* — Branch Partners PLLC; Bruce E. Black

(57) ABSTRACT

The invention concerns an orthosis (10) for stabilizing the position of the scapula (3) at least during a lateral movement of an arm (8) related to the scapula (3), comprising a torso fixation means (20), in particular a harness, fixable to the torso (2) of a person (1), and a pressure element (30) in a translational and/or pivotable way coupled to the torso fixation means (20) for applying a normal pressure force onto the scapula (3), as well as an arm fixation means (40) fixable to the arm (8), in particular to the upper arm, of the person (1), wherein the arm fixation means (40) is connected to the pressure element (30) by means of a coupling device (50) and wherein the position of connection (51) of the coupling device (50) to the pressure element (30) is realized in a distance h1 to the position of coupling (31) between the pressure element (30) and the torso fixation means (20), such that a movement of the arm (8), in particular a lifting movement (401), of a person (1) attached to the orthosis (10) is transferred by the coupling device (50) to the pressure
(Continued)

Figure 1:
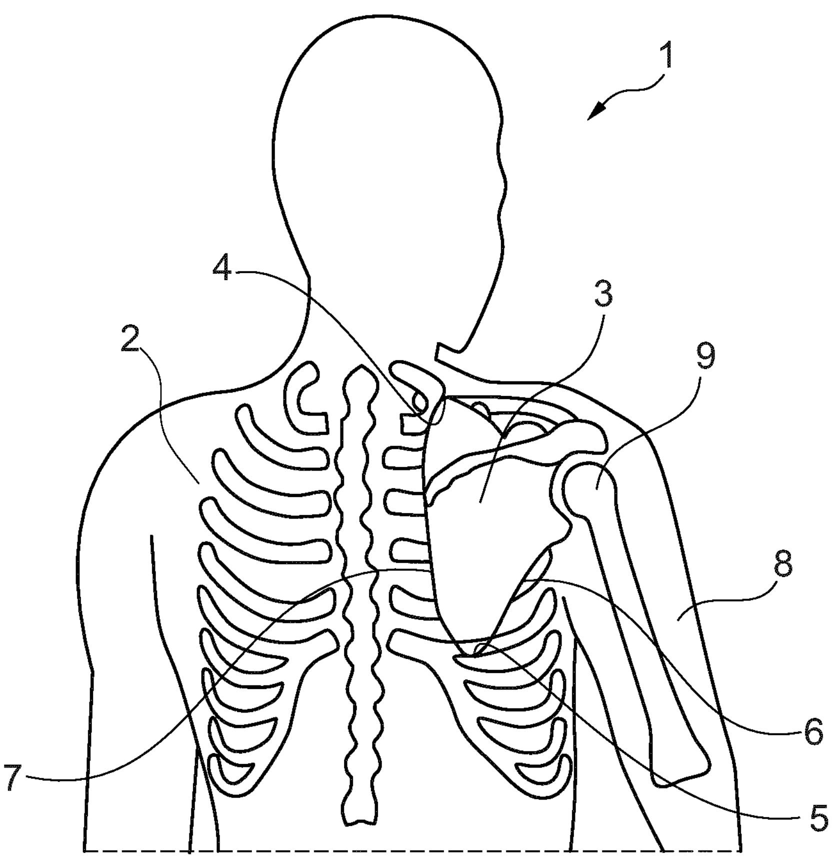

element (30) such that the pressure element (30) is moved essentially together with the scapula (3). The invention also concerns a method for stabilizing the position of the scapula (3), a system (300) for moving an arm (8) of a person (1) and a method for lifting a load (200).

20 Claims, 9 Drawing Sheets

(56) References Cited

U.S. PATENT DOCUMENTS

| | | | |
|---|---|---|---|
| 5,538,499 A * | 7/1996 | Schwenn .............. | A61F 5/3753 602/19 |
| 8,308,668 B1 | 11/2012 | Harvat | |
| 2007/0106187 A1 | 5/2007 | Campbell et al. | |
| 2012/0101419 A1* | 4/2012 | Bonutti ............... | A61F 5/05858 602/20 |
| 2014/0371644 A1 | 12/2014 | Erbe et al. | |
| 2016/0278963 A1 | 9/2016 | Webster et al. | |
| 2018/0116893 A1* | 5/2018 | Lebolt ................... | A61F 5/0104 |
| 2018/0303699 A1 | 10/2018 | Romo et al. | |
| 2020/0038218 A1* | 2/2020 | Ingvast ................ | A61B 5/1071 |

OTHER PUBLICATIONS

Extended European Search Report for EP Patent Application No. 20168373.7 mailed Sep. 7, 2020.

* cited by examiner

ORTHOSIS AND METHOD FOR STABILIZING THE POSITION OF THE SCAPULA, SYSTEM FOR MOVING AN ARM AND METHOD FOR LIFTING A LOAD

CROSS-REFERENCE TO RELATED APPLICATIONS

This present application is a U.S. national stage application of PCT Application No. PCT/EP2021/058893, filed Apr. 6, 2021, which claims priority to European Patent Application No. 20168373.7 filed Apr. 7, 2020, both of which are hereby incorporated by reference in their entirety.

The invention is related to an orthosis for stabilizing the position of the scapula as well as to a method for stabilizing the position of the scapula. It also concerns a system for moving an arm comprising an orthosis according to the invention as well as a method for lifting a load.

The kinematic interaction between the scapula and the humerus is called scapulohumeral rhythm. This interaction is important for an optimal function of the shoulder. Abnormal attitude, for example due to work, an accident or congenital malposition can cause a dysfunction of the scapulohumeral rhythm and/or a change of the normal position. One example is a scapular instability caused by a lack of tension in the muscles and ligaments attached to the scapula, causing the scapula to shift from the natural and desired pose during lifting and/or lowering the arm.

For this reason, it is desirable to support a person suffering from this malfunction while moving the arm with a device that either counteracts existing malpositions and/or prevents the development of malpositions.

On the one hand, such a device is important in the context of especially heavy physical work as a support for the working person. On the other hand, such a device can also be used in a therapeutic context, in particular to support the therapeutic staff in therapy, for example to re-establish the natural mobility of the shoulder region.

In particular from the therapeutic context, devices that support the shoulder and/or the scapula are known.

U.S. Pat. No. 3,945,376 A shows an orthopedic brace for correction of spinal deformities. The orthopedic brace shown here comprises a harness with means for supporting the scapula of the person wearing the brace. The support is realized by a pad fixed to the harness pressing onto the scapula.

U.S. Pat. No. 8,308,668 B1 discloses a medical device and a method for evaluation and treating scapulothoracic mobility disorders. The device can be positioned at the scapula for treatment of mobility disorders by the patient together with a second person.

US 2007/0106187 A1 shows a shoulder brace comprising an anterior and a posterior support member connected via a strap attachment member. The posterior support member comprises a scapular support member. The elements of the strap attachment member are partially elastic or flexible. The strap attachment member is adapted to adjust the position of the anterior and the posterior support member over the humeral head of a person to be supported by the shoulder brace.

The problem to be solved by the present invention is to provide an orthosis and a method for stabilizing the position of the scapula as well as a system and a method for lifting a load in a simple way and with a high comfort to the person.

The problem is solved by an orthosis for stabilizing the position of the scapula according to claim 1 and a method for stabilizing the position of the scapula according to claim 13.

Advantageous embodiments of the orthosis are given in the subclaims 2 to 12. In addition, the problem is solved by a system for moving an arm according to claim 14 and a method of lifting a load according to claim 15.

A first aspect of the invention is an orthosis for stabilizing the position of the scapula at least during a lateral movement of an arm related to the scapula. The orthosis comprises a torso fixation means, in particular a harness, fixable to the torso of a person, and a pressure element in a translational and/or pivotable way coupled to the torso fixation means for applying a normal pressure force onto the scapula, as well as an arm fixation means fixable to the arm, in particular to the upper arm, of the person. The arm fixation means is connected to the pressure element by means of a coupling device and the position of connection of the coupling device to the pressure element is realized in a distance h1 to the position of coupling between the pressure element and the torso fixation means, such that a movement of the arm, in particular a lifting movement, of a person attached to the orthosis is transferred by the coupling device to the pressure element such that the pressure element is moved essentially together with the scapula.

The torso fixation means is for example a harness adapted to be attached to the torso of a person. In a special embodiment the torso fixation means comprises at least two shoulder straps and at least one waist strap wherein the straps are typically textile straps. Other kinds of torso fixation means, like for example a vest, are also possible to realize a fixation to the torso of the person.

In one embodiment the torso fixation means is adapted to realize a pre-tension. One possibility is that the torso fixation means comprises torso fixation adjustment devices to adjust for example the length of the straps and/or the torso fixation means is realized by materials with a high stiffness.

The pressure element is coupled to the harness. Typically, but not necessarily, the pressure element is primarily an object extending in two dimensions, covering at least partially the scapula when the orthosis is attached to the person according to the intended use. According to the invention the expression “covering” conveys that the scapula and the pressure element extend in two essentially parallel planes, wherein the pressure element covers the scapula in a projection perpendicular to the surface of the back side of the torso of the person wearing the orthosis. In particular the pressure element covers at least 30%, in a special embodiment at least 50% of the scapula. In a very special embodiment, the pressure element covers at least 70% of the scapula. In one embodiment, the face of the pressure element facing the scapula is at least in sections shaped to adapt to the shape of the scapula and therefore adapted to realize at least partially a form fit with the scapula. The pressure element may be adapted, at least in sections, to the topology of the scapula in such a way that it can contact the shoulder blade, especially at its borders, so that the pressure element can act on the shoulder blade with feed pressures. Therefore, the pressure element may be adapted or adaptable to the specific scapula of the person. The pressure element may be made of a thermoplastic material.

The pressure element is in a translational and/or pivotable way coupled to the torso fixation means.

In case of a pivotable coupling to the torso fixation means, the pressure element is for example fixed to the torso fixation means by means of a pivot joint or hinge, wherein the position of the extension of the axis of rotation of the pivot joint is the position of coupling between the pressure element and the torso fixation means. In this embodiment the pressure element is movable in an essentially pivoting movement around the axis of rotation relative to the harness and therefore relative to the torso fixed to the harness. The extended axis of rotation of the hinge is located essentially near or in extension of the sternoclavicular joint of the person when the orthosis is attached to the person.

In case of a translational coupling to the torso fixation means, the pressure element is for example fixed to the torso fixation means by means of a linear guiding means, wherein the position of coupling between the pressure element and the torso fixation means is a medial stop of a linear guide rail which is fixed to the harness.

The linear guiding means according to this embodiment comprises typically at least a linear guide rail which is fixed at least at two points, a medial fixation point and a lateral fixation point, to the torso fixation means. Furthermore, the linear guiding means comprises a guided element which is fixed to the pressure element, wherein the guided element is in a translational way guided by the linear guide rail between a medial stop and a lateral stop. The guided element is located at a medial stop when the arm is in a lowered position and at a lateral stop when the arm is in its maximal elevated position. The medial stop and the lateral stop may be the respective medial fixation point and the respective lateral fixation point of the linear guide rail. The linear guiding means enables a translational movement of the pressure element relative to the harness and therefore to the torso fixed to the harness.

The linear guiding means is particularly beneficial for changes in plane of elevation of the arm (e.g. flexion/extension of the shoulder, anterior/posterior movement of the arm). For such arm movements the linear guide means improves the scapula guiding function of the pressure device.

In another special embodiment the guided element and/or the linear guide rail of the linear guiding means is fixed to and pivotable on the pressure element such that the pressure element is movable relative to the harness in a combined translational and pivotable movement.

The position of coupling between the pressure element and the torso fixation means is typically located essentially near the superior angle of the scapula when the orthosis is attached to a person according to the intended use and when the arm of the person is lowered.

The translational and/or pivotable coupling between the torso fixation means and the pressure element may comprise a resistance means, in particular an adjustable resistance means such that the relative movement between the pressure element and the torso fixation means is at least partially inhibited or constrained. A hinge may comprise a stiff bearing in order to realize resistance.

Furthermore, the orthosis according to the invention comprises an arm fixation means which is adapted to be fixed to the arm which is related in a functional way to the scapula to be supported by the orthosis. In particular the arm fixation means is adapted to be fixed to the upper arm. In a special embodiment the arm fixation means is realized by an arm cuff.

The arm fixation means is connected to the pressure element by means of a coupling device, which is realized by a traction device. The coupling device is connected to the pressure element at the position of connection and fixed to the arm fixation means at the position of fixation. Between the position of connection and the position of coupling a distance h1 is realized. The distance h1 corresponds typically but not necessarily to the distance between the superior angle and the inferior angle of the scapula of the person attached to the orthosis. In a special embodiment the distance h1 is adjustable in order to be adapted to the body measurements of a person or the respective application or use case.

Depending on the size of the scapula with respect to the arm geometry (cross section, volume of musculature and fat tissue) around the shoulder area, a connection point lower than the inferior angle or above may be beneficial. For example if the arm cuff cannot be located close to the glenohumeral joint, the connection point on the pressure element has to be chosen lower than the inferior point to maintain a physiological coupling of scapula movement and arm movement.

The coupling device realizes in other words a kinematic coupling between the arm fixation means and the pressure element which causes a movement of the pressure element induced by a movement of the arm, in particular a lateral arm lifting movement. Via the coupling device the movement of the arm is transferred into a pivoting and/or translational movement of the pressure element. In other words, the coupling device is adapted to apply a traction force to the pressure element such that the pressure element moves in a translational and/or pivotable way. Therefore, the traction force acting on the pressure element and causing the deflection movement may not be constant. The coupling device may be adapted to transmit an increasing or decreasing traction force depending on the position of the pressure element and/or the arm relative to the torso of the person for example by a mechanical spring element.

Typically, but not necessarily, the coupling device is adapted to transfer the arm movement in such a way that the pressure element is moved essentially in parallel to the scapula movement following the natural scapulohumeral rhythm. For example, a lateral arm movement of 30° to 50° causes a rotation of the pressure element of nearly 10° which corresponds to the natural rotation of the scapula according to the said arm lifting movement.

The pressure element is adapted to apply a normal pressure force onto the scapula, in particular while the scapula and/or the pressure element is moving. The normal pressure force is the force acting perpendicularly onto the surface of the torso and therefore onto the scapula that is covered by the pressure element. The normal pressure force causes that the scapula remains in its natural moving plane even if the muscles and ligaments attached to the scapula are debilitated.

The orthosis thus supports the scapula to follow the natural scapulohumeral rhythm by a kinematic coupling of the arm of a person to the pressure element and by the normal pressure force applied to the scapula by the pressure element. Also, the shoulder is supported and stabilized. The fixation method of the orthosis according to the invention allows a high wearing comfort for the person to be supported by the orthosis.

In one embodiment the orthosis comprises a force application means mechanically connected or connectable to the pressure element as well as to the torso fixation means, wherein the force application means comprises a tensioning device which in a tensioned state applies a force to the pressure element such that the pressure element presses essentially perpendicularly onto the scapula.

In other words, a force generated by a tensioning device of a force application means is applied to the pressure element such that a normal pressure force can be applied by the pressure element onto the scapula.

In one embodiment the force application means is mechanically fixed to the pressure element such that at least parts of the force application means are adapted to move together with the pressure element. The force to be applied to the pressure element is therefore applied essentially at the same point of normal force transmission of the pressure element independent from the respective actual position of the pressure element when the pressure element is moving. In other words, the transmission position is fixed with respect to the pressure element.

In another embodiment the force application means is indirectly mechanically connected to the pressure element such that the transmission position of the pressure element is moving when the pressure element is moving. In other words, the transmission position is essentially fixed relative to the torso but not to the pressure element.

The force application means is mechanically connected or connectable to the torso fixation means and therefore arranged or arrangeable in a fixed relation to the torso. Typically, but not necessarily, the force application means is connected by at least two distinct points on the torso fixation means. In one embodiment the force application means is connected to the torso fixation means by the tensioning device.

One point of torso fixation may be advantageously arranged close to the armpit or the shoulder of the arm to be moved.

The force application means comprises at least one tensioning device. The tensioning device can be in a tensioned state. Additionally, the tensioning device can be in a pre-tensioned state, wherein pre-tensioned means that the tensioning device is tensioned independently from an arm movement, in particular when the arm is lowered.

When the tensioning device is in a tensioned state a force is applied to the pressure element essentially perpendicularly to the side of the pressure element facing away from the scapula. The said force is caused by tensile forces acting within the tensioning device. In other words, the sum of the perpendicular components of the tensile forces acting within the tensioning device in a tensioned state is essentially the force to be applied to the pressure element.

Alternatively, the tensioning device may also be in a non-tensioned state, wherein in the non-tensioned state no force is applied to the pressure element when the arm is in a lowered position.

This embodiment of the invention provides in a tensioned state a force, in particular a constant acting force, which can be transmitted to the pressure element independent from the respective position of the pressure element when the pressure element is moved.

In a further embodiment the tensioning device comprises tensioning elements, wherein at least one tensioning element comprises at least one spring means adapted to realize at least partially the force to be applied to the pressure element.

Therefore, the tensioning elements are adapted to realize and/or hold the tensioned state and therefore are adapted to realize and/or hold the force to be applied to the pressure element.

Typically, but not necessarily, the tensioning device comprises at least two tensioning elements. In an embodiment with two tensioning elements each tensioning element is fixed to the torso at one point of torso fixation each wherein the two points of torso fixation are arranged essentially oppositely to each other. Each tensioning element extends from its point of torso fixation to the pressure element.

In another special embodiment the tensioning device comprises three tensioning elements. The tensioning elements are connected to the torso fixation means by at least one point of torso fixation each. Each tensioning element extends from its point of torso fixation to the pressure element.

The points of torso fixation are spaced in a way that the angles between the elongated extension of two adjacent tensioning elements differ by less than 50°, in particular less than 30°, when the orthosis is attached to the person and in particular when the person's arm is lowered. Therefore, the tensioning device is anchored in several directions. For example, in case of three tensioning elements the angle between two tensioning elements is between 100° and 140°. Experiments have shown that an angle close to 120° in case of three tensioning elements is close to optimum.

In an embodiment, at least one tensioning element comprises a spring means, wherein the spring means is adapted to realize a constant tensile force within the tensioning element.

Further, also the harness may be equipped with one or multiple elastic elements to modulate the overall stiffness of the tensioning element.

In one embodiment the spring means is realized by a mechanical tension spring. In another embodiment the spring means is realized by at least a section of the spring means made by an elastic deformable material, like for example an elastic strap.

In one embodiment the at least two tensioning elements comprise a section of a traction means and a redirecting means, wherein the redirecting means is partially wrapped by the section of the traction means, and wherein the section of the traction means is at least indirectly connected to the pressure element or guided by the pressure element.

A traction means is according to the invention for example a rope or cable that is redirected at the point of torso fixation by a redirecting means in a way that a section of the traction means is wrapped around the redirecting means.

On the side opposite to the point of torso fixation the section of the traction means is indirectly connected to the pressure element at a point where the pressure element is connected.

In a special embodiment the traction means is a looped rope that alternates between the points of torso fixation and the points of pressure element connection, wherein there is at each point of torso fixation and each point of pressure element connection a redirecting means to change the orientation of the looped rope. In other words, the tensioning elements are connected by the looped rope and are interrelated with respect to the tension force generated by the tensioning device.

The redirecting means can comprise a pulley or a deflection bolt to redirect the traction means by wrapping.

The points of pressure element connection may be arranged close to each other, in particular when the points of pressure element connection comprise redirecting means for redirecting the looped rope. The points of pressure element connection are arranged at the transmission position.

In a further embodiment, the points of pressure element connection may be arranged in a way so that they can rotate and/or translate with respect to the pressure means. For example, three redirecting points may be mounted on a plate so that their position towards each other is constrained. This plate is mounted to the pressure means by a pivot joint. Thereby, the plate will rotate such that it is in the equilibrium position in all poses of the pressure means. This design is beneficial to keep the changes of normal tension low during movement of the mechanism.

In a further embodiment the spring means comprises at least one compression spring applying a pressure force $F_P$ to the redirecting means such that the section of the traction means is tensioned by the redirecting means.

In other words, the section of the traction means is tensioned by a compression spring that is acting on the redirecting means. Alternatively, the spring may be a tension spring, a torsion spring or a leaf spring.

In one embodiment the compression spring is acting on a redirecting means located at a point of torso fixation and therefore away from the pressure element connection.

Alternatively or additionally, the compression spring is acting on a redirecting means located at a point of pressure element connection and therefore away from the point of torso fixation.

In a special embodiment at least one spring means comprises a scale, in particular an analog scale, wherein the redirecting means and the scale are movable relative to each other such that the tension force acting within the tensioning element can be read from the scale. Another possibility is that the spring means is adapted to measure the tension force acting within the tensioning device and to generate a digital signal.

This special embodiment allows for example a known and repeatable pre-tensioning of the orthosis according to the body measurements of the person and/or the intended special use case of the orthosis.

In another embodiment the tensioning device comprises an adjusting means adapted to adjust the length of the section of the traction means so that by means of the adjusting means the length of the sections of the traction means is adjustable, in particular to generate a pre-tensioning force of the tensioning elements.

In other words, the adjusting means allows to pre-tension the orthosis by adjusting the length of at least one section of at least one of the traction means. Therefore, the adjusting means allows to adapt the orthosis to the body measurements of the person to be supported by the orthosis and/or to using it in the intended special use case.

It is not excluded that the tensioning device comprises an adjusting means for each tensioning element, to tension each section of the traction means separately and independently.

The adjusting means is typically but not necessarily arranged at a point of torso fixation, in particular arranged within reach of the person and is adapted to tension all tensioning elements at the same time or by the same adjusting action.

In another embodiment the adjusting means is arranged in a central position between the tensioning elements, in particular between the points of torso fixation. In particular, the adjusting means is replacing a redirecting means of a tensioning element.

It is not excluded that the adjusting means is located at a distance to the pressure element at the torso fixation means, wherein the adjusting means is at least indirectly connected to the pressure element for example by a bowden cable system. In a special embodiment the adjusting means is at least indirectly connected to a point of torso fixation, while the location of the adjusting means is within reach of the person.

The adjusting means may comprise a rotary mechanism that is adapted to tension the tensioning element by shortening an effective length of at least one section of the traction means by winding it up. Alternatively, the adjusting means may also comprise for example a clamping mechanism.

The adjusting means may comprise the points of pressure element connection such that in case of a looped rope the rope is alternating between the adjusting means and the points of torso fixation realized by redirecting means. In this embodiment the adjusting means connects several tensioning elements. In particular all tensioning elements are connected by the adjusting means and can be pre-tensioned by it.

The position of the adjusting means relative to the pressure element can be fixed in particular at the transmission position of the pressure element such that the adjusting means is mechanically fixed to the pressure element. In particular the adjusting means is fixed to the pressure element in a pivotable way such that the adjusting means has one degree of rotation freedom and is pivotable relative to the pressure element, when the pressure element is moving according to an arm movement of the person.

This embodiment allows to pre-tension the orthosis due to the body measurements of the person to be supported by the orthosis and/or due to the special use case of the orthosis.

The adjusting means may be realized such that the pre-tensioning force of the tensioning elements is adjustable by hand. In other embodiments the adjusting means may comprise an electrical or pneumatical actuator for adjusting the pre-tensioning force.

In one embodiment the force application means comprises a transfer element at least partially overlapping the pressure element and adapted to press on the pressure element.

The tensioning device is connected to the transfer element such that the force to be applied to the pressure element is transferable from the tensioning elements via the transfer element to the pressure element. The size and shape of the pressure element and the transfer element, which are movable relative to each other in essentially parallel planes, match in such a way that the transfer element is at least partially overlapping the pressure element in a lowered position as well as in a lifted position of the arm.

The transfer element is typically mechanically connected to the tensioning elements such that the tensile force of the tensioning element in a tensioned state acts on the transfer element. The mechanical connection can be realized indirectly by the adjusting means being mechanically fixed to the transfer element.

Typically, but not necessarily, the transfer element is primarily an object extending in two dimensions, covering at least partially the pressure element when the orthosis is attached to the person according to the intended use of the orthosis. According to the invention the expression "covering" conveys that the pressure element and the transfer element extend in two essentially parallel planes, wherein the transfer element covers the pressure element in an overlapping area of a projection perpendicular to the surface of the back side of the torso of the person wearing the orthosis.

In particular the transfer element covers at least 30%, in a special embodiment at least 50% of the pressure element, when the arm of the person is in a lowered position. In a very special embodiment, the transfer element covers at least 70% of the pressure element, when the arm of the person is in a lowered position.

The transfer element may not be directly fixed to the pressure element such that the transfer element and the pressure element are movable relative to each other, wherein the position of the transfer element relative to the torso fixation means and therefore relative to the torso of the person is essentially fixed and the pressure element is movable in a plane between the transfer element and the body of the person.

The size and the shape of the transfer element and the pressure element match in such a way that the transfer element is at least partially overlapping the pressure element in a lowered position as well as in a lifted position of the arm.

In other words, even when the arm of the person is laterally lifted such that the angle between the arm and the torso is less than 180°, in particular less than 120°, or in particular less than 90°, and the pressure element is deflected according to this arm movement, in particular by the same deflection angle of the scapula following the natural scapulohumeral rhythm, the transfer element is still at least partially covering the pressure element.

Therefore, even when the arm is laterally lifted the transfer element still transmits at least partially the tensile force of the tensioning elements to the pressure element such that the pressure element acts with a normal pressure force onto the scapula.

To reduce the frictional force between the pressure element and the transfer element the surfaces of the pressure element and/or the transfer element facing each other are at least partially covered by a low friction material combination. For example, the surface of the transfer element and/or pressure element that is facing the respective other element is covered by Polytetrafluorethylen. Alternatively, a sliding layer may be arranged between the transfer element and the pressure element.

Other possible materials to reduce frictional forces are Teflon, materials pairing a hard polished surface and a soft low friction surface, e.g. microfiber textile, steel, Polyoxymethlyen (POM), dry or lubricated.

In another embodiment the coupling device is a rope adjustable regarding length in order to adjust the length of the coupling device with respect to the body measurements of the person to be attached to the orthosis and/or is an elastic rope in order to apply a force to the pressure element such that the pressure element presses onto the scapula in a tensioned state of the elastic rope.

The coupling device is in other words a traction device adapted to transmit the arm movement to the pressure element to move the pressure element together with the scapula. By the coupling device a traction force is applied to the pressure element that moves the pressure element in a translational and/or pivotable way according to the arm movement.

The coupling device can be a rope that is adjustable regarding its length between the position of fixation at the arm fixation means and the position of connection to the pressure element. This length can also be called the effective length.

In order to move the pressure element by the arm according to the natural scapulohumeral rhythm the effective length between the position of fixation and the position of connection may be adjusted according to the body measurements of the person to be supported by the orthosis.

Alternatively or additionally, the coupling device is an elastic rope, wherein the rope is in particular elastic in a section between the position of fixation and the position of connection. Elasticity may be realized by one or more spring elements arranged in a row and/or parallel between the position of fixation and the position of connection.

The spring elements may have different or same spring constants.

In a further embodiment, for each spring element a means to restrict the maximum extension may be arranged in parallel to the respective elastic element. This design is a means to control the elongation/force ration of the coupling device.

By the rope, in particular by the elastic rope, additionally to the tensioning device a force is applied to the pressure element, when the rope is tensioned.

In a further embodiment the distance h1 between the position of coupling between the pressure element and the torso fixation means and the position of connection of the coupling device to the pressure element is related to a distance h2 between a position of fixation of the coupling device at the arm fixation means and the position of a humeral head of the arm of the person wearing the orthosis by the ratio h2/h1, wherein h2/h1 is at least 0.15 and at most 0.7, in particular at least 0.25 and at most 0.4.

The position of a humeral head of the arm of the person is in particular the position of the glenohumeral joint.

At a ratio h2/h1 of nearly 0.33 in the orthosis according to the invention the pressure element is movable essentially parallel to the scapula according to the natural scapulohumeral rhythm. Depending on the person or the special use case it may be advantageous to realize ratios h2/h1 that differ from the ratio 0.33.

In another embodiment a distance h3 between the position of fixation of the coupling device at the arm fixation means and the position of connection of the coupling device to the pressure element is related to the distance h1 by the ratio h3/h1, wherein h3/h1 is at least 0.3 and at most 1, in particular at least 0.5 and at most 0.8, when the arm of the person wearing the orthosis is in an essentially laterally lifted position.

Further, a distance h5 between the position of coupling and the humeral head may be the same or bigger as the distance h3 between the position of fixation of the coupling device at the arm fixation means and the position of connection of the coupling device to the pressure element, wherein h3<sqrt(h1^2+(h5+h2)^2).

In a special embodiment is h3<h5 as long as h3>h5+h2−h1.

The distance h3 defines indirectly the angle between the arm of the person and the torso of the person, at which the coupling device, in particular the effective length of the coupling device is first tensioned when the person is laterally lifting the arm. In other words, it defines the largest angle between the arm of the person and the torso of the person at which no traction force is working on the pressure element and the pressure element is therefore not moving. Is the person lifting the arm even higher the traction force is deflecting the pressure element. Therefore, the distance h3 may also be called the activating distance.

In another embodiment the orthosis comprises a retracting device fixed to the pressure element that is adapted to apply a restoring force $F_{Rest}$ on the pressure element. The direction of action of the restoring force is opposite to a translational and/or pivotable deflection movement of the pressure element provoked by an essentially lateral arm lifting movement such that the pressure element is movable by the restoring force $F_{Rest}$ essentially a direction opposite to the deflection movement when the arm is lowered.

The retraction device comprises a retraction mechanism and typically at least one spring means to realize the restoring force. The direction of action of the restoring force $F_{Rest}$ according to this embodiment may be realized by a deflection means which deflects the effective direction of the restoring force $F_{Rest}$ such that the restoring force is acting essentially in an extension but opposite to the traction force of the coupling device, in particular when the arm is laterally lifted and therefore the rope of the coupling device is tensioned. In case the traction force is lower than the restoring force $F_{Rest}$ provided by the retracting means, the pressure element is moved in medial direction. In case the traction force is higher than the restoring force $F_{Rest}$ provided by the retracting means, the pressure element is moved in lateral direction.

In one embodiment the retraction force $F_{Rest}$ is realized by a spring means wherein the spring means is adapted to provide a retraction force $F_{Rest}$ between 5N and 20N. In particular, a retraction force $F_{Rest}$ of 10N may be provided.

The actual retraction force $F_{Rest}$ depends on the friction of the overall mechanism and the lever of the retraction force with respect to the rotation/pivot point of the pressure mechanism.

The spring means best implements a very low stiffness and a high pretension, such that the change in retraction force F_Rest is small over the whole travel.

It is in general possible to adjust the restoring force $F_{Rest}$ of the retracting means by a restoring adjustment means such that the restoring force $F_{Rest}$ can be adapted to the person attached to the orthosis and/or to the special use case of the orthosis.

The advantage of this embodiment is that the pressure element is pulled back to its normal and undeflected position when the arm is lowered in particular such that the pressure element moves in parallel to the scapula.

It is not excluded to realize a retraction device directly coupled to the arm fixation means. For example, the retraction means can be realized by an antagonistic rope fixed to the arm fixation means and at a medial border of the pressure element wherein the antagonistic rope is redirected at a redirection element arranged at the shoulder of the person to be supported by the orthosis.

In another embodiment the pressure element has at least one protrusion on its scapula facing side adapted to rest against a side of the scapula so that by the protrusion a feeding force $F_{Feed}$ directed essentially perpendicularly to the normal pressure force is applied to the scapula when the arm is moved.

A protrusion according to the invention can also be realized by a bent border section of the pressure element.

The protrusion is adapted to rest at least against a section of the medial and/or lateral side of the scapula. To realize a comfortable attachment between the scapula and the pressure element the protrusion may be adapted or adaptable to the person to be attached to the orthosis.

In one special embodiment the pressure element comprises a first protrusion on its scapula facing side adapted to rest against a lateral border of the scapula so that by the first protrusion a feeding force in medial direction is applied to the scapula when the pressure element is moved by the restoring force $F_{Rest}$.

Alternatively or additionally, the pressure element comprises a second protrusion on its scapula facing side adapted to rest against a medial side of the scapula so that by the second protrusion a feeding force in lateral direction is applied to the scapula when the arm is lifted and the lifting movement is transmitted by the coupling device. By the coupling device, in particular by the rope of the coupling device, a traction force is applied to the pressure element acting in this special embodiment by the second protrusion on the medial side of the scapula and therefore moves the pressure element in a translational and/or pivotable way together with the scapula.

The feeding force in lateral direction and/or the feeding force in medial direction acts essentially perpendicularly to the normal pressure force applied to the scapula.

Therefore, the respective protrusion supports the respective movement of the pressure element by applying a feeding force in medial and/or lateral direction to the scapula.

Furthermore, the orthosis may comprise a limiting element that is adapted to limit the deflection movement of the pressure element.

In one embodiment the pivot joint at the position of coupling comprises a limiting element which restricts the rotary movement around the rotation axis of the pivot joint in one and/or both directions of rotation. The possible degree of the rotational deflection may be adjustable by the limiting element.

In another embodiment the linear guiding means, in particular the guiding rail, comprise at least one limiting element to restrict the translational deflection movement of the pressure element. The possible way of the translational deflection may be adjustable by the limiting element.

In another embodiment the retracting device comprises a limiting element, to limit the deflection movement of the pressure element when the arm is lifted.

It is not excluded that the force applied onto the scapula is at least partially generated by a pneumatically, hydraulically, electro-chemically, chemically or thermally pressurizing mechanism connected to the pressure element.

A second aspect of the invention is a method for stabilizing the position of the scapula at least during a lateral movement of an arm related to the scapula, in particular when lifting loads by a lateral lifting movement of the arm and/or by a lateral abduction combined with horizontal abduction/adduction, of a person provided with an orthosis according to the invention, wherein the orthosis is provided and attached to the person such that the torso fixation means, in particular the harness, is fixed to the torso of the person and the arm fixation means is fixed to the arm, in particular to the upper arm, of the person and the arm is lifted in an essentially lateral arm movement wherein a normal pressure force is applied to the scapula by the pressure element.

Attaching the orthosis to the person may include pretensioning the tensioning elements of the tensioning device. Attaching the orthosis may also include in at least some embodiments adjusting the length of the coupling device according to the person's body measurements and/or the special use case. Attaching may also include to adjust limiting elements that restrict the movement of the pressure element to a certain range.

The method supports a person's scapula when lifting loads such that the natural scapula movement is supported and impairments due to physical work, in particular to lifting heavy loads, are prevented.

A third aspect of the invention is a system for moving an arm of a person comprising a driving device for moving an arm of a person, in particular for lifting an arm of a person, and an orthosis according to the invention.

The driving device may be part of an exoskeleton, that supports the arm movement or drives the arm movement of a person.

In one embodiment the driving device may be connected to the arm fixation means and/or the torso fixation means such that an integrated system comprising the driving device as well as the orthosis is realized.

The orthosis according to the invention supports the movement of the scapula in its natural plane while the driving device is moving the arm of the person or is supporting the movement of the arm of the person.

It is not excluded that the orthosis may be combined with a therapeutically driving device. A further aspect of the invention is a method for lifting a load by a lateral lifting movement of an arm of a person, wherein a system for moving an arm of a person according to the invention is attached to a person, and wherein the driving device is operated such that the arm of the person is lifted and a normal pressure force is applied to the scapula by the pressure element of the orthosis.

The invention is explained below using the embodiment examples shown in the enclosed drawings.

It is shown in

Figure 2:
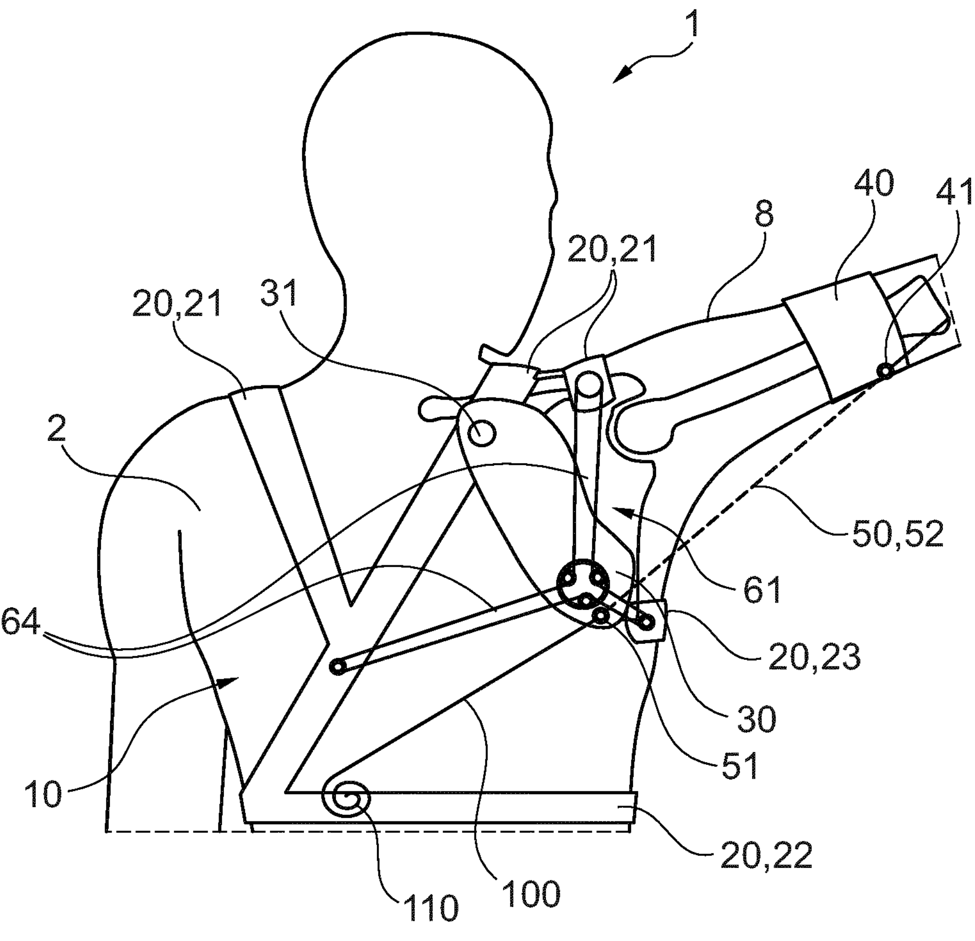
Figure 3:
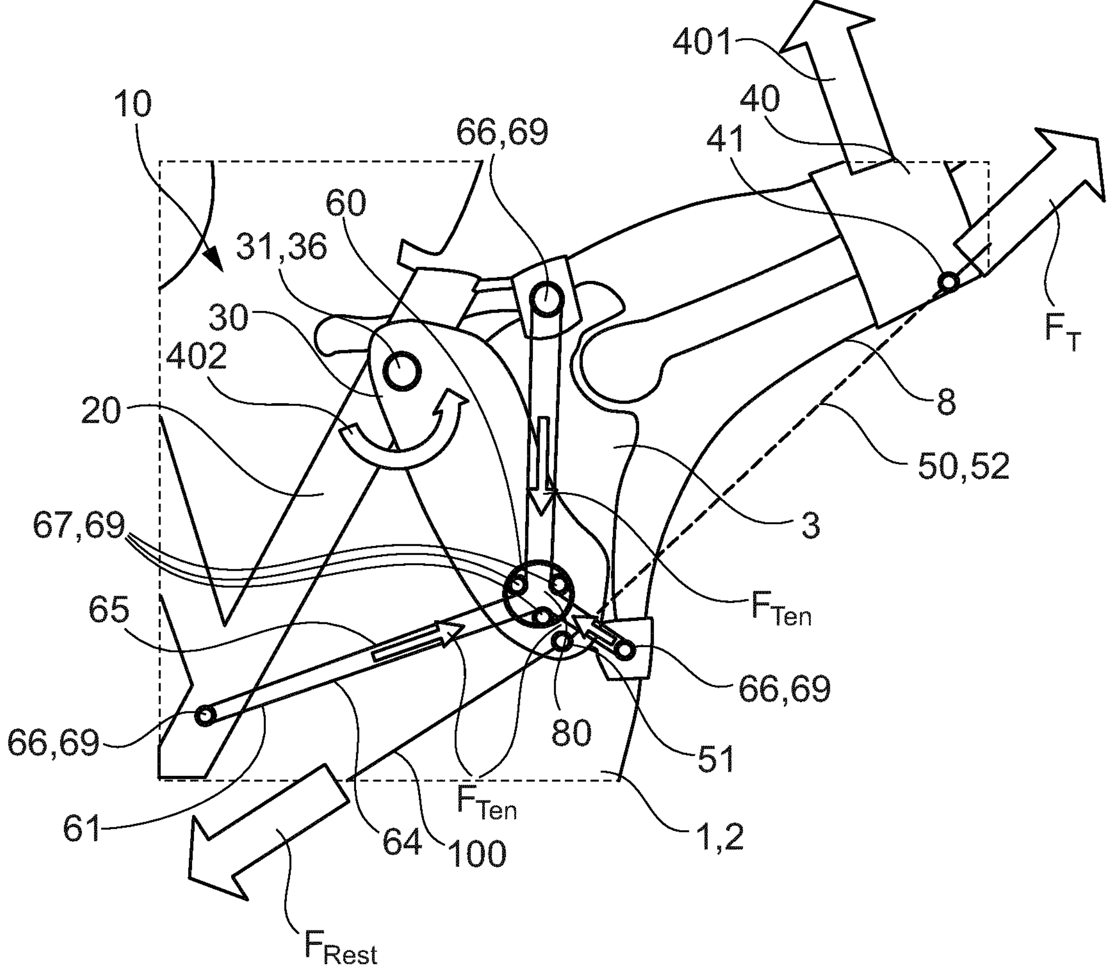
Figure 4:
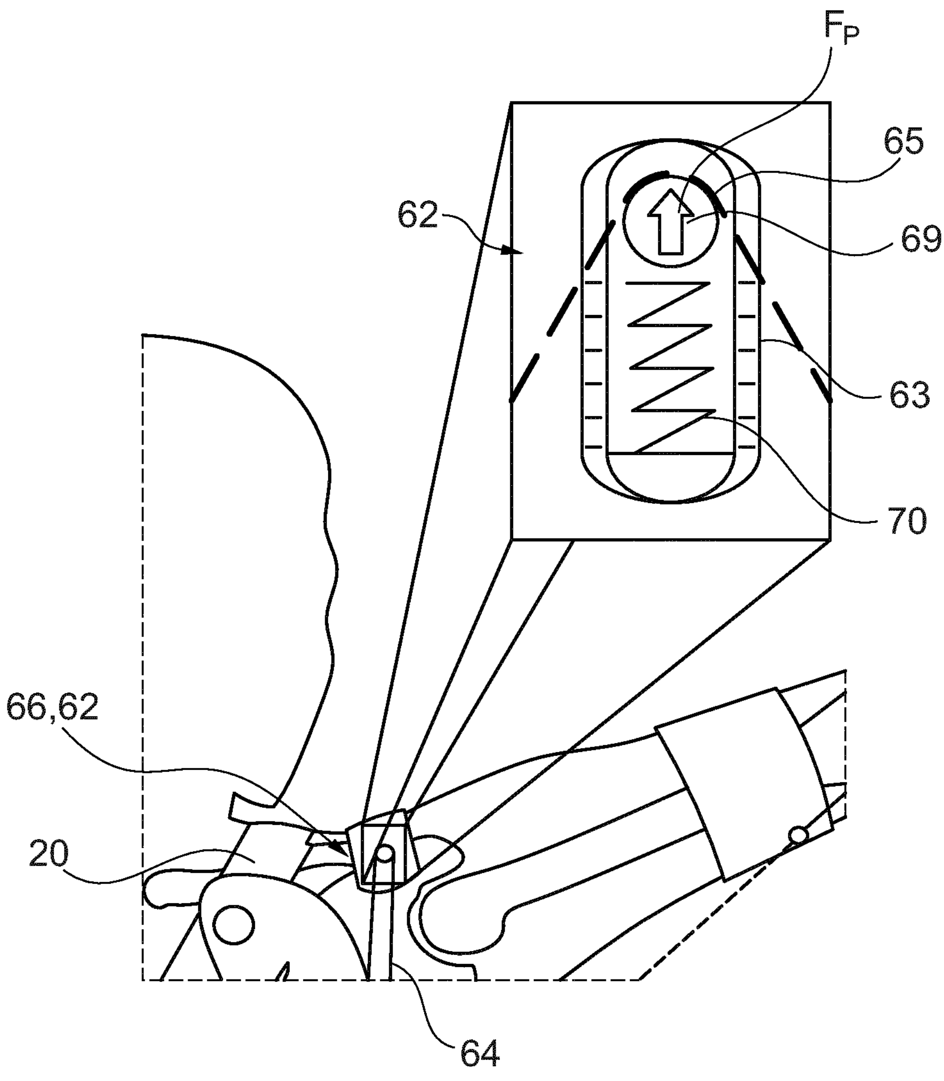
Figure 5:
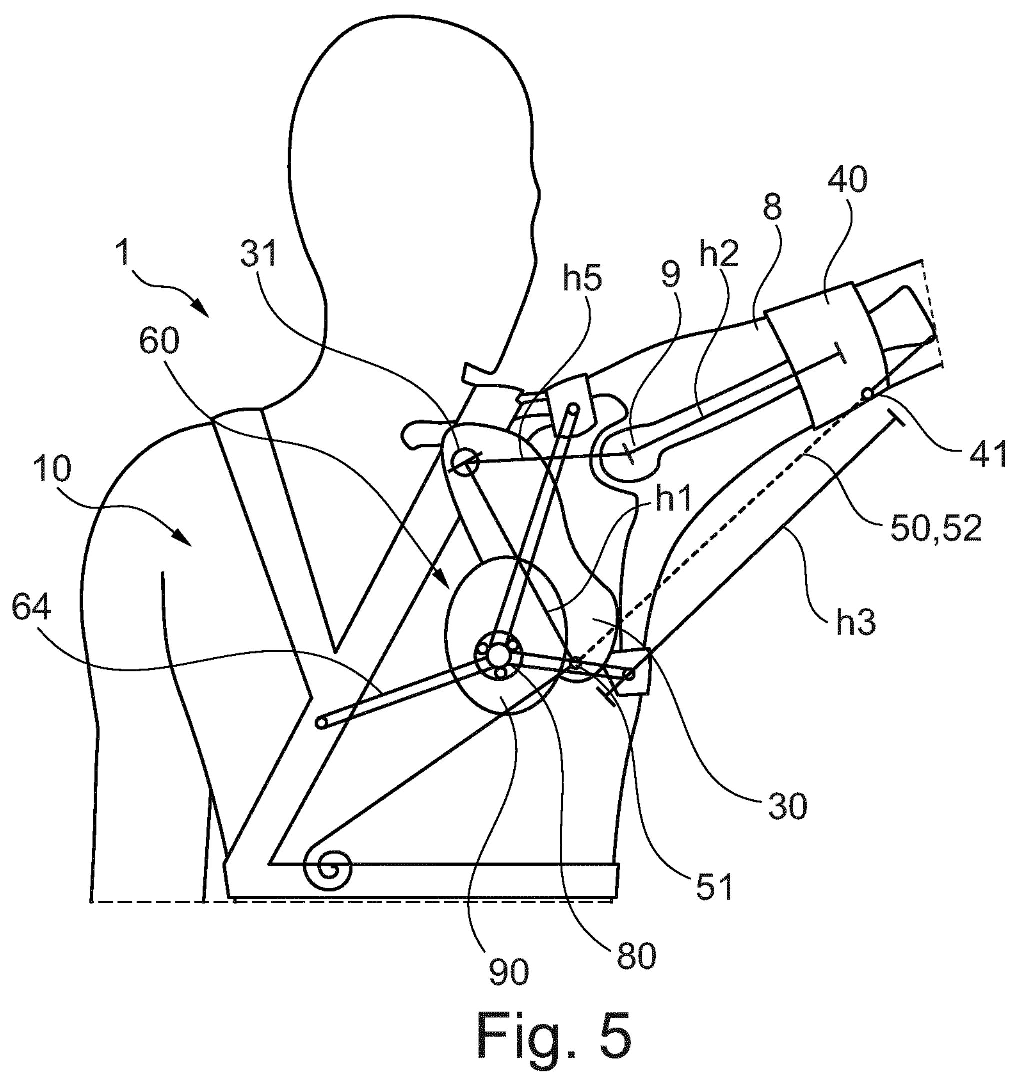
Figure 6:
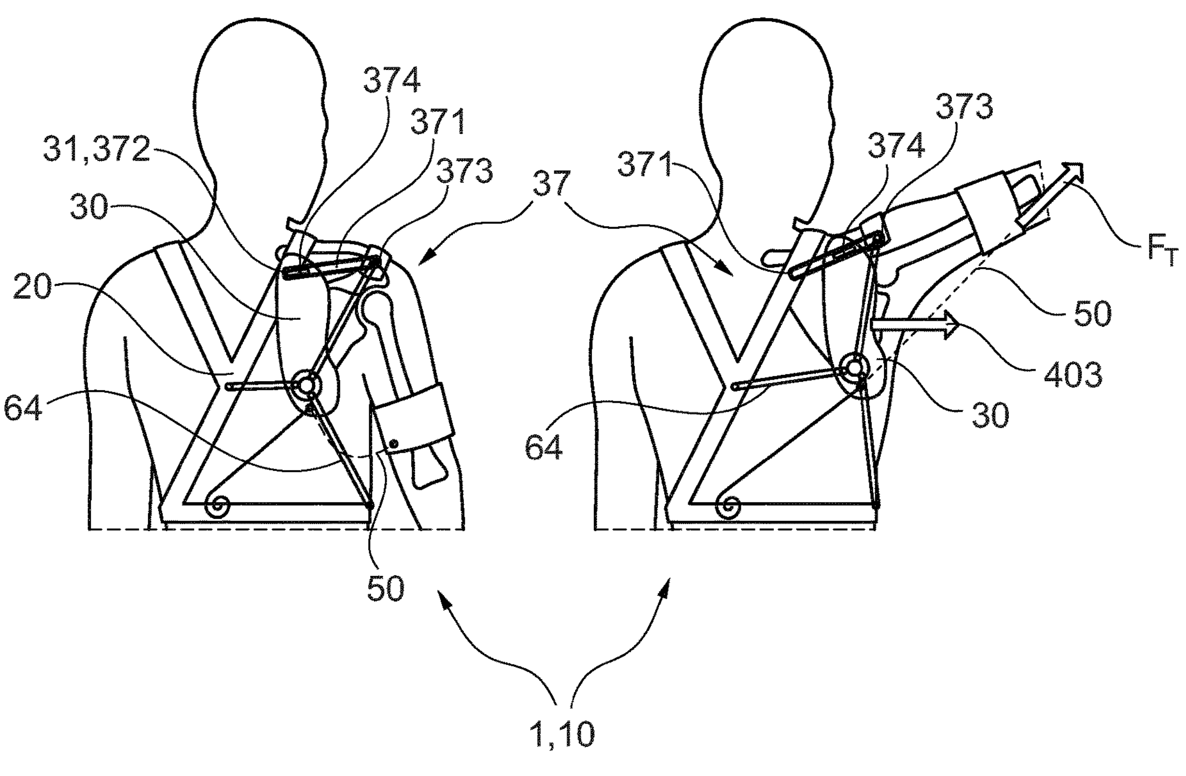
Figure 7:
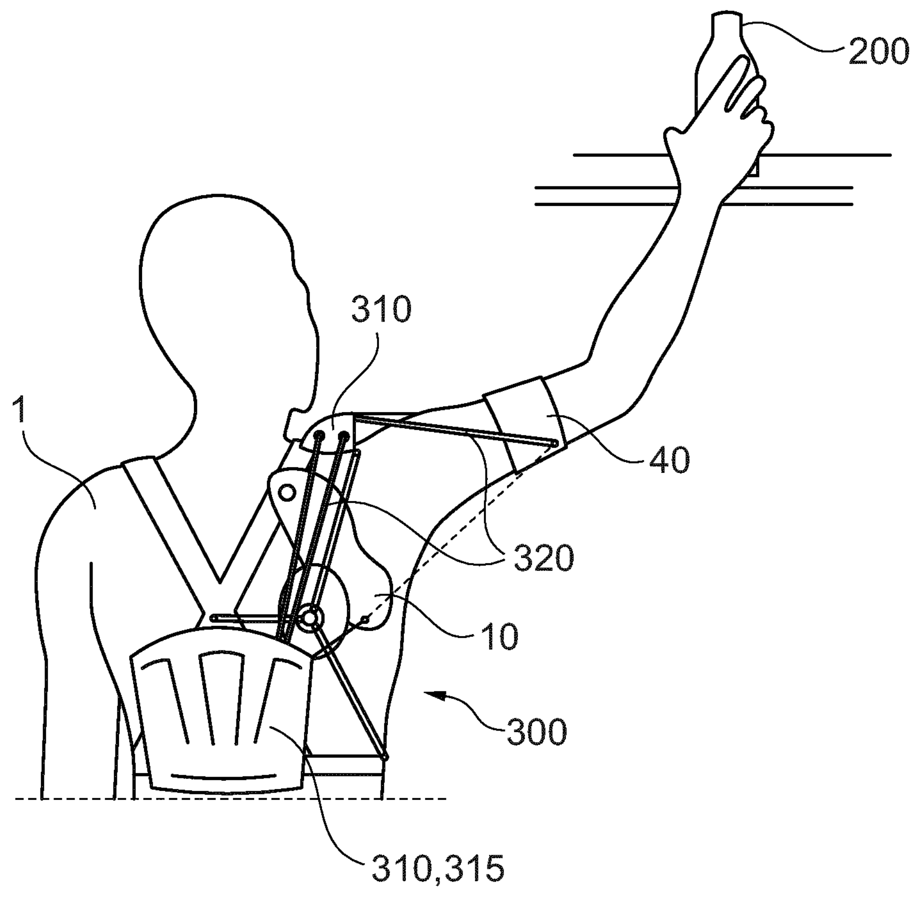
Figure 8:
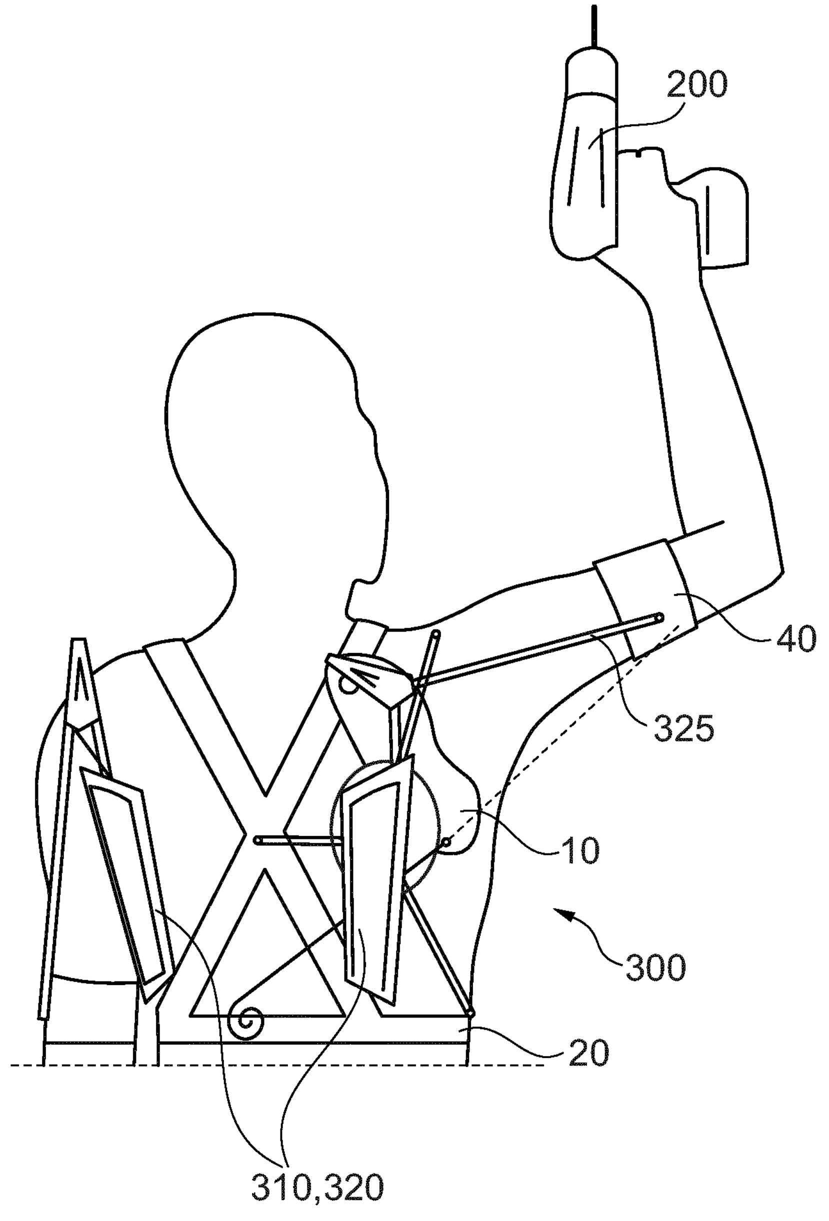
Figure 9:
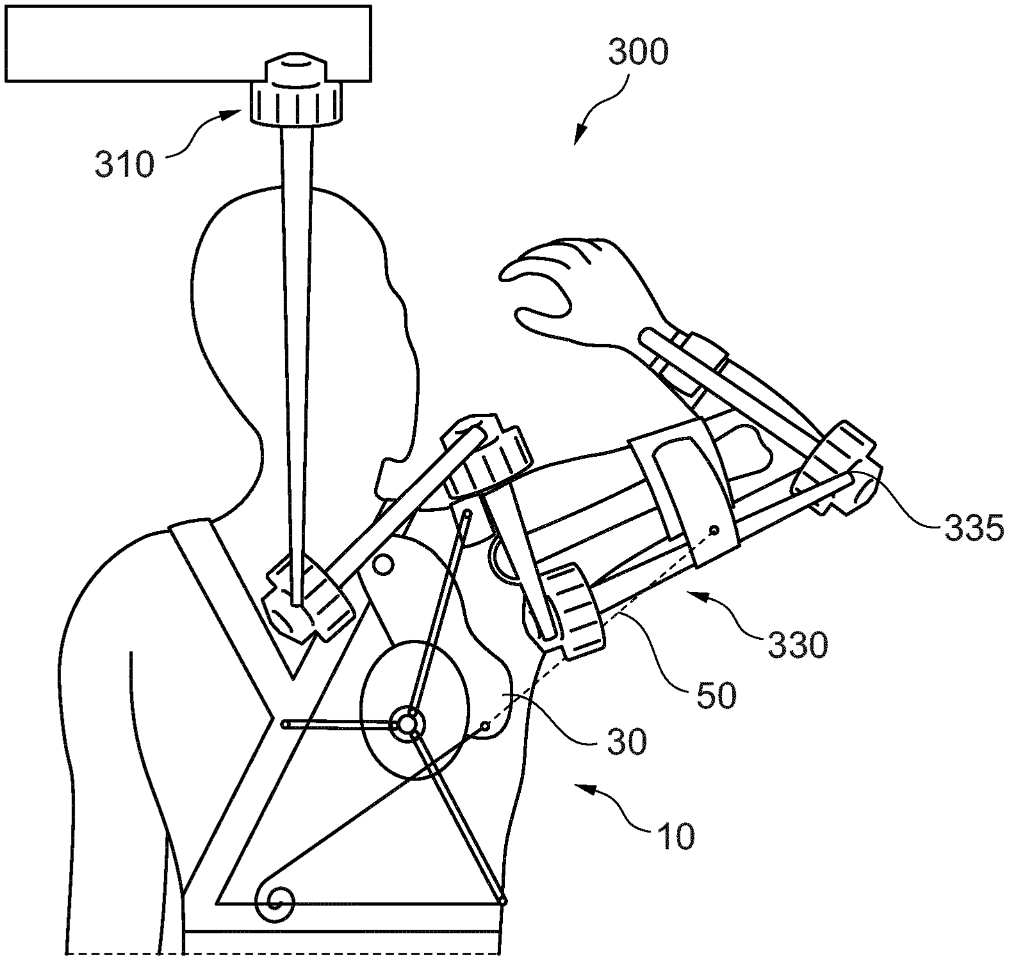

FIG. 1: the back side of a torso of a person,

FIG. 2: an embodiment of the orthosis according to the invention attached to a person, FIG. 3: the embodiment of the orthosis of FIG. 2 in detail, FIG. 4: an embodiment of the spring means of a tensioning element, FIG. 5: an embodiment of the orthosis according to the invention comprising a transfer element, FIG. 6: another embodiment of the orthosis according to the invention attached to a person, FIG. 7: a first embodiment of the system for moving an arm, FIG. 8 a second embodiment of the system for moving an arm, and FIG. 9: a third embodiment of the system for moving an arm.

To give an overview of the relevant anatomy of a person 1, FIG. 1 shows the back side of a torso 2 of a person 1. The orthosis according to the invention is adapted to support the scapula 3 of the person 1 to follow the natural scapulohumeral rhythm. The scapula 3 comprises a lateral scapula border 6, a medial scapula border 7, a superior angle 4 and an inferior angle 5. It is also shown in FIG. 1 the arm 8 of the person 1 to be lifted and the humeral head 9.

FIG. 2 shows an embodiment of the orthosis 10 according to the invention attached to a person 1, wherein the arm 8 of the person 1 is in a laterally lifted position. The angle between the arm 8 and the torso 2 is that wide that the rope 52 of the coupling device 50 is tensioned.

FIG. 2 shows one embodiment of the torso fixation means 20. In the example given here the torso fixation means 20 comprises several shoulder straps 21, one chest strap 23 and one waist strap 22. At the position of coupling 31 the pressure element 30 is connected to the torso fixation means 20 in a pivotable way, in particular to one of the shoulder straps 21 that is arranged on the right side of the torso 2 which is the side of the torso 2 where the person's scapula has to be supported in this example.

The orthosis 10 shown here has a tensioning device 61 comprising three tensioning elements 64 that are mechanically connected to the torso fixation means 20 as well as to the pressure element 30. The pressure element 30 is connected to an arm fixation means 40 by a coupling device 50. The coupling device 50 is in the example shown here a rope 52 that is connected to the arm fixation means 40 at the position of fixation 41 and to the pressure element 30 at the position of connection 51. The orthosis 10 also comprises a retraction device 100 with a mechanical spring 110.

The tensioning elements 64 are in a tensioned state so that a force is applied to the pressure element 30 such that the pressure element 30 presses with a normal pressure force onto the scapula.

FIG. 3 shows the embodiment of the orthosis 10 of FIG. 2 in detail. When the person 1 being attached to the orthosis 10 is lifting the arm 8 in an essentially lateral arm lifting movement 401 such that a certain angle between the arm 8 and the torso 2 is exceeded the rope 52 of the coupling device 50 is tensioned and a traction force $F_T$ is acting on the pressure element 30. The rope 52 is fixed to the arm fixation means 40 at the position of fixation 41 and fixed to the position of connection 51 of the pressure element 30. In other words, the coupling device 50 realizes a kinematic coupling between the arm fixation means 40 and the pressure element 30. By the traction force $F_T$ the pressure element 30 is rotated around the rotation axis at the position of coupling 31, realized in the given example by a pivot joint 36, between the pressure element 30 and the torso fixation means 20 in a rotation movement 402. The pressure element 30 is rotating essentially in a plane parallel to the scapula 3. The length of the rope 52 between the position of fixation 41 and the position of connection 51 defines at which angle between the arm 8 and the torso 2 the pressure element 30 starts rotating.

The pressure element 30 is pressing with a normal pressure force onto the scapula 3. The normal pressure force is generated by a force application means 60. The force application means 60 comprises a tensioning device 61 with three tensioning elements 64 each comprising a section of the traction means 65 wrapped around the redirecting means 69. The traction means 65 is in the given example a looped rope altering between six redirecting means 69. Three redirecting means 69 are fixed to the torso fixation means 20 at the points of torso fixation 66 and three redirecting means 69 that are fixed to the pressure element 30 at the points of pressure element connection 67. The points of pressure element connection 67 are part of the adjusting means 80. The adjusting means 80 is fixed to the pressure element 30 and therefore moves together with the pressure element 30 in a rotation movement 402 when the arm 8 of the person 1 is lifted.

The adjusting means 80 is adapted to pre-tension the traction means 65 and therefore the tensioning elements such that a tension force $F_{Ten}$ is acting within the force application means 60 and in particular within the tensioning elements 64.

In the opposite direction to the traction force $F_T$ a restoring force $F_{Rest}$ is acting on the pressure element 30. When the person 1 is lowering the arm 8 the restoring force $F_{Rest}$ is pulling back the pressure element 30 in medial direction.

FIG. 4 shows an embodiment of the spring means 62 of a tensioning element 64. The spring means 62 shown here is arranged at a point of fixation 66 of the tensioning element 64 on the shoulder of the person. The enlargement of the detail shows that a section of the traction means 65 is wrapped around a redirecting means 69. The spring means 62 comprises a compression spring 70 that is pressing with a pressure force $F_P$ against the redirecting means 69 and therefore tensions the traction means 65. The redirecting means 69 is movable relative to a scale 63 such that the pre-tensioning is quantifiable. The scale 63 is fixed relative to the torso fixation means 20.

FIG. 5 shows an embodiment of the orthosis 10 according to the invention comprising a transfer element 90 attached to a person 1 with the arm 8 in a lifted position. The force application means 60 comprises, besides three tensioning elements 64 and an adjusting means 80 like in FIGS. 2 and 3, a transfer element 90. The adjusting means 80 is fixed to the transfer element 90. The three tensioning elements 64 are fixed to the adjusting means 80. The transfer element 90 is not fixed to the pressure element 30. When the arm 8 is lifted the pressure element 30 is moved relative to the transfer element 90. The transfer element 90 stays essentially in its position relative to the torso of the person 1.

FIG. 5 shows that the size and shape of the pressure element 30 and the transfer element 90 are such that the pressure element 30 is covered by the transfer element 90 in a lowered position of the arm 8 as well as in a lifted position of the arm 8. The tension force within the tensioning elements 64 essentially stays the same when the arm 8 is moved because the tensioning elements 64 are via the adjusting means 80 indirectly fixed to the transfer element 90. The transfer element 90 is acting with an essentially constant force on the pressure element 30.

FIG. 5 also shows the distance h1 between the position of coupling 31 and the position of connection 51, the distance h2 between the position of fixation 41 and the humeral head 9 and the distance h3 between the position of fixation 41 and the position of connection 51 as well as the distance h5 between the position of coupling 31 and the humeral head 9. The ratio h2/h1 and h3 as well as the ratio h3/h1 are adjustable for example by the length of the rope 52 of the coupling device 50 between the position of fixation 41 and the position of connection 51 and/or by the position of the arm fixation means 40. Via the ratio h2/h1 and h3 as well as the ratio h3/h1 the orthosis is adaptable to the body measurements of the person 1 and the special use case of the orthosis 10. That is, in particular h3 is adapted to the body anatomy to couple the rotation of the pressure means with the humerus movement.

FIG. 6 shows another embodiment of the orthosis 10 according to the invention attached to a person 1. Contrary to the embodiments shown before, this embodiment shows a translational coupling between the torso fixation means 20 and the pressure element 30. On the left-hand side the person 1 attached to the orthosis 10 is shown with a lowered arm. On the right-hand side the person 1 is shown with a lifted arm. It can be seen that the traction force $F_T$ causes a translational movement 403 of the pressure element 30 via the coupling device 50.

In this embodiment the coupling between torso fixation means 20 and pressure element 30 is realized by a linear guiding means 37 with a linear guide rail 371 that is fixed at a medial fixation point 372 and a lateral fixation point 373 at the torso fixation means 20. The linear guide rail 371 is guiding a guided element 374 that is fixed to the pressure element 30. The medial fixation point 372 is located at the position of coupling 31.

This embodiment comprises three tensioning elements 64 directly fixed to the pressure element 30. It is also possible to realize a translational movement of the pressure element 30 combined with the use of a transfer element.

FIG. 7 shows a first embodiment of the system 300 for moving an arm. The person 1 being attached to the system 300 shown in FIG. 7 is lifting a load 200 with an arm lifting movement. The movement of the arm is at least partially realized by a driving device 310 that is connected to the arm fixation means 40. In another embodiment the driving device may be attached to the arm by another connection means than the fixation means.

In the example shown here in FIG. 7 the back plate 315 comprises an actuator like for example an electric motor. While the arm is lifted by the pulling means 320 into a lifted position the orthosis 10 is supporting the scapula of the person 1 to move in its natural rhythm in its natural plane. This embodiment of the system 300 can be realized with flexible material and may be integrated in clothing with high wearing comfort.

FIG. 8 shows a second embodiment of the system 300 for moving an arm for lifting a load 200. Contrary to FIG. 7 the driving device 310 shown here is less flexible. For moving the arm the driving device 310 is coupled to the arm fixation means 40 by bars 325 that are movable by pressure springs 320 not shown here in detail.

In another embodiment the driving device may be attached to the arm by another connection means than the fixation means.

Wherein FIG. 7 and FIG. 8 show two examples of the system 300 with the person 1 being connected to the system 300 but wherein the person 1 is freely movable together with the system 300, FIG. 9 shows a third embodiment of the system 300 with a person being integrated into a fixed rod system 330 with several actuators 335. The arm of the person is connected to the rod system 330 and therefore movable by a driving device 310. In the example shown here the coupling device 50 is connected to the rod system 330 such that the rod system 330 is moving the pressure element 30 as well.

LIST OF REFERENCE SIGNS

1 person
2 torso
3 scapula
4 superior angle
5 inferior angle
6 lateral scapula border
7 medial scapula border
8 arm
9 humeral head
10 orthosis
20 torso fixation means
21 shoulder strap
22 waist strap
23 chest strap
30 pressure element
31 position of coupling
36 pivot joint
37 linear guiding means
40 arm fixation means
41 position of fixation
50 coupling device
51 position of connection
52 rope
60 force application means
61 tensioning device
62 spring means
63 scale
64 tensioning elements
65 traction means
66 points of torso fixation
67 point of pressure element connection
69 redirecting means
70 compression spring
80 adjusting means
90 transfer element
100 retracting device
110 mechanical spring
200 load
300 system
310 driving device
315 back plate
320 pulling means
325 bar
320 pressure spring
330 system of rods
335 actuator
371 linear guide rail 372 medial fixation point
373 lateral fixation point
374 guided element
401 lifting movement
402 rotation movement
403 translation movement
h1 distance
h2 distance
h3 distance
h5 distance
$F_T$ traction force
$F_P$ pressure force
$F_{Ten}$ tensile force
$F_{Rest}$ restoring force

The invention claimed is:

1. Orthosis for stabilizing a position of a scapula at least during a lateral movement of an arm related to the scapula comprising a torso fixation means fixable to the torso of a person, and a pressure element in a translational and/or pivotable way coupled to the torso fixation means for applying a normal pressure force onto the scapula, as well as an arm fixation means fixable to the arm of the person, wherein the arm fixation means is connected to the pressure element by means of a coupling device, wherein the orthosis is configured for the lateral movement of the arm, and wherein the position of connection of the coupling device to the pressure element is realized in a distance h1 to the position of coupling between the pressure element and the torso fixation means, such that the lateral movement of the arm of a person attached to the orthosis is transferred by the coupling device to the pressure element such that the pressure element is moved essentially together with the scapula.

2. Orthosis for stabilizing the position of the scapula as claimed in claim 1, characterized in that the orthosis comprises a force application means mechanically connected or connectable to the pressure element as well as to the torso fixation means, wherein the force application means comprises a tensioning device which in a tensioned state applies a force to the pressure element such that the pressure element presses essentially perpendicularly onto the scapula.

3. Orthosis for stabilizing the position of the scapula as claimed in claim 2, characterized in that the tensioning device comprises tensioning elements, wherein at least one of the tensioning elements comprises at least one spring means adapted to realize at least partially the force to be applied to the pressure element.

4. Orthosis for stabilizing the position of the scapula as claimed in claim 3, characterized in that at least two of the tensioning elements comprise a section of a traction means and a redirecting means, wherein the redirecting means is partially wrapped by the section of the traction means, and wherein the section of the traction means is at least indirectly connected to the pressure element.

5. Orthosis for stabilizing the position of the scapula as claimed in claim 4, characterized in that the at least one spring means comprises at least one compression spring applying a pressure force $F_P$ to the redirecting means such that the section of the traction means is tensioned by the redirecting means.

6. Orthosis for stabilizing the position of the scapula as claimed in claim 4, characterized in that the tensioning device comprises an adjusting means adapted to adjust the length of the section of the traction means so that by means of the adjusting means the length of the section of the traction means is adjustable.

7. Orthosis for stabilizing the position of the scapula as claimed in claim 6, wherein the length of the sections of the traction means is adjustable to generate a pre-tensioning force of the tensioning elements.

8. Orthosis for stabilizing the position of the scapula as claimed in claim 3, characterized in that the force application means comprises a transfer element at least partially overlapping the pressure element and adapted to press on the pressure element, wherein the tensioning device is connected to the transfer element such that the force to be applied to the pressure element is transferable from the tensioning elements via the transfer element to the pressure element, and wherein the size and shape of the pressure element and the transfer element, which are movable relative to each other in essentially parallel planes, match such in a way that the transfer element is at least partially overlapping the pressure element in a lowered position as well as in a lifted position of the arm.

9. Orthosis for stabilizing the position of the scapula as claimed in claim 1, characterized in that the coupling device is a rope adjustable regarding length in order to adjust the length of the coupling device with respect to the body measurements of the person to be attached to the orthosis and/or is an elastic rope in order to apply a force to the pressure element such that the pressure element presses onto the scapula in a tensioned state of the elastic rope.

10. Orthosis for stabilizing the position of the scapula as claimed in claim 1, characterized in that the distance h1 between the position of coupling between the pressure element and the torso fixation means and the position of connection of the coupling device to the pressure element is related to a distance h2 between a position of fixation of the coupling device at the arm fixation means and the position of a humeral head of the arm of the person wearing the orthosis by the ratio h2/h1, wherein h2/h1 is at least 0.15 and at most 0.5.

11. Orthosis for stabilizing the position of the scapula as claimed in claim 10, wherein h2/h1 is at least 0.25 and at most 0.4.

12. Orthosis for stabilizing the position of the scapula as claimed in claim 1, characterized in that a distance h3 between the position of fixation of the coupling device at the arm fixation means and the position of connection of the coupling device to the pressure element is related to the distance h1 by the ratio h3/h1, wherein h3/h1 is at least 0.3 and at most 1, when the arm of the person wearing the orthosis is in an essentially laterally lifted position.

13. Orthosis for stabilizing the position of the scapula as claimed in claim 1, characterized in that the orthosis comprises a retracting device fixed to the pressure element that is adapted to apply a restoring force $F_{Rest}$ on the pressure element, wherein the direction of action of the restoring force $F_{Rest}$ is opposite to a translational and/or pivotable deflection movement of the pressure element provoked by an essentially lateral arm lifting movement, such that the pressure element is movable by the restoring force $F_{Rest}$ essentially in a direction opposite to the deflection movement when the arm is lowered.

14. Orthosis for stabilizing the position of the scapula as claimed in claim 1, characterized in that the pressure element has at least one protrusion on its scapula facing side adapted to rest against a side of the scapula so that by the at least one protrusion a feeding force $F_{Feed}$ directed essentially perpendicularly to the normal pressure force is applied to the scapula when the arm is moved.

15. Orthosis for stabilizing the position of the scapula as claimed in claim 1, wherein the torso fixation means is a harness.

16. Orthosis for stabilizing the position of the scapula as claimed in claim 1, wherein the arm fixation means is fixable to an upper arm of the person.

17. Orthosis for stabilizing the position of the scapula as claimed in claim 1, wherein the lateral movement of the arm is a lifting movement.

18. Method for stabilizing the position of the scapula at least during the lateral movement of an arm related to the scapula of a person provided with an orthosis according to claim 1, wherein the orthosis is provided and attached to the person such that the torso fixation means is fixed to the torso of the person and the arm fixation means is fixed to the arm of the person and the arm is lifted in essentially the lateral arm movement wherein a normal pressure force is applied to the scapula by the pressure element.

19. System for moving an arm of a person, comprising a driving device for moving an arm of a person and an orthosis according to claim 1.

20. Method for lifting a load by a lateral lifting movement of an arm of a person, wherein a system for moving an arm of a person according to claim 19 is attached to a person, and wherein the driving device is operated such that the arm of the person is lifted and a normal pressure force is applied to the scapula by the pressure element of the orthosis.

* * * * *